(12) United States Patent
Jacobs et al.

(10) Patent No.: US 6,306,625 B1
(45) Date of Patent: Oct. 23, 2001

(54) METHOD FOR OBTAINING EXPRESSION OF MIXED POLYPEPTIDE PARTICLES IN YEAST

(75) Inventors: Eric Jacobs; Apolonia Rutgers, both of Brussels (BE)

(73) Assignee: SmithKline Beecham Biologicals, Sa, Rixensart (BE)

(*) Notice: Subject to any disclaimer, the term of this patent is extended or adjusted under 35 U.S.C. 154(b) by 0 days.

(21) Appl. No.: 08/823,578

(22) Filed: Mar. 25, 1997

Related U.S. Application Data (63) Continuation of application No. 08/498,545, filed on Jul. 5, 1995, now abandoned, which is a continuation of application No. 08/329,354, filed on Oct. 26, 1994, now abandoned, which is a continuation of application No. 08/170,610, filed on Dec. 21, 1993, now abandoned, which is a continuation of application No. 08/028,037, filed on Mar. 8, 1993, now abandoned, which is a continuation of application No. 07/846,487, filed on Feb. 28, 1992, now abandoned, which is a continuation of application No. 07/368,401, filed on Jun. 19, 1989, now abandoned, which is a continuation-in-part of application No. 07/292,202, filed on Dec. 30, 1988, now abandoned.

(51) Int. Cl.$^7$ .................................................. C12N 15/09
(52) U.S. Cl. .................... 435/69.9; 435/69.3; 435/71.1; 435/254.11; 435/254.21; 435/254.2; 435/254.23; 424/227.1
(58) Field of Search ............................ 435/5, 69.3, 69.1, 435/69.9, 70.1, 71.1, 254.21, 172.3, 254.11, 320.1, 254.2, 254.23, 255.1, 255.2, 255.5, 255.6, 227.1

(56) References Cited

U.S. PATENT DOCUMENTS

| | | | |
|---|---|---|---|
| 4,722,840 | * | 2/1988 | Valenzuela et al. . |
| 4,769,238 | | 9/1988 | Rutter et al. ............................ 424/89 |
| 4,818,527 | * | 4/1989 | Thornton et al. . |
| 4,963,483 | * | 10/1990 | Ellis et al. . |

FOREIGN PATENT DOCUMENTS

| | | | |
|---|---|---|---|
| 0 198 474 | 10/1986 | (EP) | ............................. C12N/15/00 |
| WO 88/01646 | 3/1988 | (WO) | ............................. C12N/15/00 |

OTHER PUBLICATIONS

Tiollais et al., "The hepatitis B virus", *Nature*, 317, pp. 489–495 (1985).

Heermann et al., "Large Surface Proteins of Hepatitis B Virus Containing the Pre–s Sequence", *J. Virol.*, 52, No. 2 pp. 396–402 (1984).

Eble et al., "Hepatitis B Surface Antigen: an Unusual Secreted Protein Initially Synthesized as a Transmembrane Polypeptide", *Mol. Cell. Biol.*, 6, No. 5, pp. 1454–1463 (1986).

Ou et al., "Regulation of Secretion of the Hepatitis B Virus Major Surface Antigen by the PreS–1 Protein" *J. Virol.*, 61, No. 3.: pp. 782–786 (1987).

Valenzuela et al., "Construction of plasmids and expression of HBsAg in Yeast" *Nature*, 298, pp. 348–350 (1982).

Valenzuela et al., "Synthesis and Assembly in Yeast of Hepatitis B Surface Antigen Particles Containing The Polyalbumin Receptor", *Biotech*, 3, pp. 317–320 (1985).

Itoh et al., "Express of Hepatitis B Virus Surface Antigen P31 Gene in Yeast," *Biochem. and Biophys. Res. Comm.*, 138, No. 1 pp. 268–274 (1986).

Langley et al., "Characterization of purified hepatitis B surface antigen containing pre–S(2) epitopes expressed in *Saccharomyces cerevisiae*", *Gene*, 67 pp. 229–245 (1988).

Rutgers et al., "Expression of Different Forms of Hepatitis B Virus Envelope Proteins in Yeast", *Viral Hepatitis and Liver Disease*, ed. A. J. Zuckerman, A. R., Liss, New York, pp. 304–308 (1988).

Rutgers et al., "Hepatitis B Surface Antigen as Carrier Matrix for the Repetitive Epitope of the Circumsporozoite Protein of *Plasmodium falciparum*", *Biotech.*, 6, pp. 1065–1070 (1988).

Kingsman et al., "Heterologous Gene Expression in *Saccharomyces cerevisiae*", *Biotechnology and Genic Engineering Reviews*, 3, pp. 377–416 (1985).

Mohamad et al., "Baculovirus Expression System to Study the Assembly of HBV in Insect Cells: Co–Expression of the Three HBV Envelope Proteins Results in their Co–Assembly and Secretion as HBsAg Particles", *Abstracts*, Meeting of Hepatitis B Viruses, Cold Spring Harbor Laboratory, Cold Spring Harbor, NY p. 27 (1987).

Streeck et al., "Expression and Modification of Hepatitis B Surface Antigen", *J. Cell. Biochem.*, 12B Suppl., p. 6 (Abstract F010) (1988).

Dehoux et al., "Expression of the hepatitis B virus large envelope protein in *Saccharomyces cerevisiae*", *Gene*, 48, pp. 155–163 (1986).

Jacobs et al., "Simultaneous Synthesis of the Hepatitis B Surface Antigens in *Saccharomyces Cerevisiae* and Assembly as "Mixed Particles" Similar to those Found in the Sera of Infected Persons", 14th Int. Conf on Yeast Genetics and Molecular Biology, p. E17 (1988).

Imamura et al., "Expression of Hepatitis B Virus Middle and Large Surface Antigen Genes in *Saccharomyces cerevisiae*" *J. Virol.*, 61 No. 1, pp. 3543–3549 (1987).

Kniskern et al., "A Candidate Vaccine for Hepatitis B Containing the Complete Viral Surface Protein" *Hepatol.* 8 No. 1, pp. 82–87 (1988).

(List continued on next page.)

Primary Examiner—Laurie Scheiner
(74) Attorney, Agent, or Firm—Zoltan Kerekes; Stephen Venetianer; Charles M. Kinzig (57) ABSTRACT

The present invention provides a method for obtaining expression of a mixed hepatitis B surface antigen particle, e.g., a particle of mixed polypeptide composition, in yeast. Also disclosed is a method for obtaining multimeric structures presenting two or more polypeptides by expression in yeast as fusion proteins with the S antigen of HBsAg.

19 Claims, 2 Drawing Sheets

OTHER PUBLICATIONS

Jin et al., "Human T Cell Response to the Surface Antigen of Hepatitis B Virus (HBsAg)", *J. Exp. Med.*, 168, pp. 293–306 (1988).

Cregg et al., "*Pichia pastoris* as a Host System for Transformations" *Mol. Cell. Biol.* 5 No. 12, pp. 3376–3385 (1985).

Schneider et al., "Rosettes from Friend Leukemia Virus Envelope: Preparation and Physicochemical and Partial Biological Characterization", *J. Virol.*, 29, pp. 624–632 (1979).

Schneider et al., "Purification of Murine and Feline Type–C Virus Envelope Polypeptides as Micellar Protein Complexes", *Z. Naturforsch*, 36 c, pp. 353–356 (1981).

Schneider et al., "Virosomes Constructed from Lipid and Purified Friend Leukaemia Virus Glycoprotein", *J. Gen. Virol.*, 64, pp. 559–565 (1983).

Tamura et al., "Subunit Structure of Islet–Activating Protein, Pertussis Toxin, in Conformity with the A–B Model", *Biochem.*, 21, pp. 5516–5522 (1982).

Jingdong, "Heterologous Gene Expression in *Sacharomyces Cerevistae* Using a Dominant Selection and Amplification System", "Thesis from the University of Ghent", Belgium (1986–87).

Milich et al., "Immune Response to the Pre–S(1) Region of the Hepatitis B Surface Antigen (HBsAg): A Pre–S(1)–Specific T Cell Response can Bypass Nonresponsiveness to the Pre–S(2) and S Regions of HBsAg", *J. of Immunology*, 137 No.(1), pp. 315–322 (1986).

Milich et al., "Antibody production to the nucleocapsid and envelope of the hepatitis B virus primed by a single synthetic T cell site" *Nature*, 329, pp. 547–549 (1987).

Neurath et al., "Antibodies to a synthetic peptide from the preS 120–145 region of the hepatitis B virus envelope are virus–neutralizing", *Vaccine*, 4, pp. 35–37 (1986).

Neurath et al., "Identification and Chemical Synthesis of a Host Cell Receptor Binding Site on Hepatitis B Virus", *Cell*, 46, pp. 429–436 (1986).

Towler et al., "The Biology and Enzymology of Eukaryotic Protein Acylation", *Ann. Rev. Biochem.*, 57, pp. 69–99 (1988).

Itoh et al., "A synthetic peptide vaccine involving the product of the pre–S(2) region of hepatitis B virus DNA: Protective efficacy in chimpanzees", *Proc. Natl. Acad. Sci. USA*, 83, pp. 9174–9178 (1986).

Itoh et al., "Synthesis in Yeast of Hepatitis B Virus Surface Antigen Modified P31 Particles by Gene Modification", *Biochem. and Biophy. Res. Comm.* 141, No. 3, pp. 942–948 (1986).

Machida et al., "A Polypeptide Containing 55 Amino Acid Residues Coded by the Pre–S Region of Hepatitis B Virus Deoxyribonucleic Acid Bears the Receptor for Polymerized Human as Well as Chimpanzee Albumins", *Gastroenterology*86, pp. 910–918 (1984).

Persing et al., "The preS1 Protein of Hepatitis B Virus Is Acylated at Its Amino Terminus with Myristic Acid", *J. of Virology*, 61 No. 5, pp. 1672–1677 (1987).

Suihko et al., "Signal Recognition Particle from *S. pombe*" 14th Int. Conf. on Yeast Genetics and Mol. Biol., (1988).

* cited by examiner

METHOD FOR OBTAINING EXPRESSION OF MIXED POLYPEPTIDE PARTICLES IN YEAST

This is a continuation of application Ser. No. 08/498,545, filed Jul. 5, 1995, now abandoned which is a continuation of application Ser. No. 08/329,354, filed Oct. 26, 1994, now abandoned, which is a continuation of Ser. No. 08/170,6 10, filed Dec. 21, 1993, now abandoned, which is a continuation of Ser. No.08/028,037 filed Mar. 8, 1993, now abandoned, which is a continuation of Ser. No. 07/846,487 filed Feb. 28, 1992, now abandoned, which is a continuation of Ser. No. 07/368,401, filed Jun. 19 , 1989, now abandoned, which is a continuation-in-part of Ser. No. 07/292,202 filed Dec. 30, 1988, now abandoned.

FIELD OF THE INVENTION

This invention refers generally to the construction of yeast strains synthesizing simultaneously different heterologous proteins or polypeptides. More specifically the invention refers to the production of hepatitis B surface antigen particles by introducing two or more vectors, each carrying an individual polypeptide expression cassette into a single yeast cell and allowing assembly of the mixed (composite) particle.

BACKGROUND OF THE INVENTION

Hepatitis B virus (HBV) infection in humans is associated with the occurrence in the serum of various structures carrying the hepatitis B surface antigen (HBsAg) [Tiollais et al, *Nature,* 17:489 (1985)]. In addition to infectious virions, filamentous and spherical particles of 22 nm in diameter (containing about 100 envelope proteins) are present which are formed by association of host-derived lipids with the three hepatitis surface proteins: the major (S), middle (M) and large (L) proteins. These proteins share the same sequence of 226 amino acids on the HBV genome, known as the S protein coding sequence. The entire 163 amino acid coding sequence which immediately precedes the S protein coding sequence on the HBV genome is referred to herein as the preS coding sequence. The middle protein includes the additional 55 amino acid amino-terminal region (preS2 region) which immediately precedes the S protein (M protein: 55 plus 226 amino acids). The large protein includes the remaining 108 amino acid region (preS1 region) of the preS coding sequence (L protein: 108 plus 55 plus 226 amino acids). See, Heermann et al, *J. Virol.,* 52:396 (1984).

Because the promoter for the S and M specific transcripts is embedded within the open reading frame of the L protein, transformation of mammalian cells with DNA encoding the complete open reading frame for the L protein may result in synthesis of all three surface proteins. In mammalian cells, HBsAg particles are secreted [reviewed by Tiollais et al, *Nature,* 17:489 (1985)]. However, an overproduction of L protein relative to S protein leads to an inhibition of secretion of HBsAg particles [See, e.g., Ou et al, *J. Virol.,* 61:782 (1987)].

In yeast, transcription initiation is directed by the 5' yeast promoter sequence and viral transcription initiation signals within the HBV genes are not functional. For that reason, expression of the genes encoding the S, M or L protein in yeast leads in each case to only one primary translation product. The S protein, the M protein and the L protein have been expressed independently by several laboratories [See, e.g., Valenzuela et al, *Nature,* 298:347 (1982); Valenzuela et al, *Biotech.,* 3:317 (1985); Itoh et al, *Biochem. Biophys. Res. Comm.,* 138:268 (1986) and others].

Glycosylation of the surface proteins produced in *S. cerevisiae* differs from glycosylation observed in mammalian cells. The major protein is not glycosylated, whereas the middle and the large protein are produced in N- and O-linked glycosylated and non-glycosylated forms. N-linked chains of the high mannose type were identified, as well as O-linked oligosaccharide chain(s) [See, Itoh, et al, cited above; Langley et al, *Gene,* 67:229 (1988)]. When extracted from yeast, both the S and M protein are recovered as lipoproteic particles closely resembling the 22 nm particle present in serum of human HBV patients. The L protein was also recovered in lipoproteic structures, but their exact nature was not elucidated [See, Rutgers et al, "Viral Hepatitis and Liver Disease", ed. A. J. Zuckerman, A. R. Liss, New York, pp. 304–308 (1988)].

HBsAg particles have been used as carrier matrices for presentation of foreign epitopes by fusing heterologous sequences within the preS2 region, leading to particles with the heterologous epitopes exposed at their surface. In one instance, it was shown that the presentation resulted in improved immunogenicity. [Valenzuela et al, *Biotech.,* 3:323 (1985); Rutgers et al, *Biotech.,* 6:1065 (1988)].

S. M. Kingsman et al, *Biotech. Gen. Eng. Rev.,* 3:377 (1985) refers to expression of heterologous genes in *S. cerevisiae,* including HBsAg in unglycosylated form. This document also refers to the *S. cerevisiae* Ty element for use in multicopy chromosomal integrative vectors.

Rutter et al, U.S. Pat. No. 4,769,238 refers to the synthesis of HBsAg in yeast and the construction of an expression vector containing the S protein but excluding the 163 amino acid presequence.

Valenzuela et al, U.S. Pat. No. 4,722,840 refers to hybrid polypeptides formed of an HBsAg fragment fused to a heterologous amino acid sequence defining an epitopic site of a pathogen or toxin. The presurface polypeptide of HBsAg links the particle forming and heterologous sequences.

A. A. Mohamad et al, Abstracts, Meeting on Hepatitis B. Viruses, Cold Spring Harbor Laboratory, Cold Spring Harbor, N.Y., p. 27 (1987) refers to expression of HBsAg particles in a baculovirus expression system. The particles are believed to be of the S or M HBV proteins in glycosylated and unglycosylated form, the L protein in both forms, or particles having all three proteins.

R. E. Streeck et al, *J. Cell Biochem.,* 12B Suppl., 6 (Abstract F010) (1988) refers to insertion of sequences, e.g. for poliovirus type 1, into the S gene of HBV and expression in mammalian cells of mixed particles containing HBs-Polio-Ag and HBsAg.

European Patent Application 0,198,474 refers to expression in bacterial cells of plasmids carrying the $PreS_1$-$PreS_2$-S protein coding region of HBsAg.

PCT Application WO88/01646 refers to a recombinant DNA containing a transposase, a control sequence and transposable element enabling the insertion of exogenous DNA into prokaryotic and eukaryotic cells.

Although vaccines presently described and in use have great efficacy, a certain percentage of persons receiving such vaccines, particularly immunocompromised persons, e.g., hemodialysis patients, are non- or slow responders [See, e.g., Hadler et al, *New Engl. J. Med.,* 315:209–215 (1986); and Bruguera et al, *PostGrad. Med. J.,* 63:155–158 (1987)].

Thus, there remains a need in the art for methods and compositions useful in preparing additional effective vaccines to HBV.

BRIEF DESCRIPTION OF THE DRAWINGS

FIGS. 1 and 2 are a schematic diagram of vector pRIT12927 and of the Ty integrative vector described in Example 1. LTR means Ty1 "long terminal repeat". Restriction sites are identified as follows: S for SalI, X for XhoI, B for BglII; E for EcoRI. Parentheses indicate restriction sites that are destroyed in constructions. Thin lines represent pBR322 sequences or linkers. The second schematic shows the pRIT12927 derivative vector with a selective marker and gene of interest inserted between the SalI sites of the Ty sequence.

SUMMARY OF THE INVENTION

In one aspect, the invention provides a method for obtaining expression of a novel hepatitis B surface antigen (HBsAg) particle of mixed polypeptide composition in yeast. The method entails coexpressing in a yeast cell a first protein S, and a second protein X-S, where S represents substantially the major surface protein of hepatitis B virus (HBV) and X represents preS1S2 or preS2 or one or more other polypeptides. Optionally a third protein Y-S and other additional proteins may also be coexpressed with the first protein S according to this method, with Y and the other additional proteins being preS1S2 and preS2 or one or more other, polypeptides.

In one embodiment, the method involves transforming a selected yeast cell with a first vector carrying an S protein expression cassette, and a second vector carrying the X-S expression cassette. In another embodiment of this method a third vector carrying the Y-S expression cassette may be cotransformed therewith. The vectors may be successively integrated and achieve the coexpression and assembly of the S, X, and optional Y polypeptides by homologous recombination within the yeast cell. Preferred vectors for use in such a method are Ty expression vectors described in detail below. Alternatively, other Ty transposable vectors may be used to accomplish the coexpression and assembly by the mechanism of transposition within the yeast cell. Still another alternative method of the invention employs compatible conventional plasmid or phage vectors to carry the desired expression cassettes and transform the yeast host cell.

The method of the invention thus permits the assembly of HBsAg particles of mixed composition, i.e., an assembly of polypeptides carrying different heterologous epitopes, or other functional domains, in a single HBsAg particle. These particles present several foreign epitopes, or other functional domains, in well defined relative amounts at the surface of one HBsAg particle for use as vaccine components.

As another aspect of the present invention there is provided a mixed HBsAg particle, i.e., a multimeric assembly of two or more different polypeptides including the S protein of HBsAg, or a multimeric assembly of the S protein with one or more hybrid polypeptides into a particulate structure of mixed polypeptide composition (e.g., S and X-S, Y-S and the like). For example, the mixed particle can contain the S and the M protein of HBsAg, the S and the L protein from HBsAg, the S, M and L proteins from HBsAg, or can also contain modified S, M and L proteins. Alternatively, X or Y can represent an immunoprotective epitope, a B cell epitope, or a T cell helper cell epitope or cytotoxic T cell epitope of a pathogenic microorganism, virus, or other cell.

Still a further aspect of this invention are vaccines comprising a mixed, composite particle of the present invention, alone or in combination with other vaccinal agents and pharmaceutically acceptable vaccinal carriers and adjuvants. These mixed particles of the present invention thus broaden the spectrum of antibodies against HBV, and may provide an earlier response to viral challenge by the person vaccinated with the vaccines containing these proteins. Additionally the vaccines containing these particles may enable persons who do not respond to S protein to mount a preS response, or may augment or enhance the S response.

Other aspects and advantages of the present invention are described in the following detailed description.

DETAILED DESCRIPTION OF THE INVENTION

The invention provides a method for obtaining expression of a mixed HBsAg particle of mixed polypeptide composition.

For ease in reference, the following Table I sets out the DNA coding sequences and amino acid sequences for the preS1, preS2 and S regions of the HBV proteins discussed herein; amino acid numbers are above the codons in parentheses. These coding sequences are from an HBV adw subtype, which was isolated from plasmid pRIT10616. This plasmid, harbored in E. coli K12 strain 600, is on deposit at the American Type Culture Collection, Rockville, Md., U.S.A. under accession number ATCC# 38131.

TABLE I

PRE-S1 REGION

```
NcoI
(12)
ATG GGG ACG AAT CTT TCT GTT CCC AAC CCT CTG GGA TTC TTT
Met Gly Thr Asn Leu Ser Val Pro Asn Pro Leu Gly Phe Phe (26)
CCC GAT CAT CAG TTG GAC CCT GCA TTC GGA GCC AAC TCA AAC
Pro Asp His Gln Leu Asp Pro Ala Phe Gly Ala Asn Ser Asn
```

TABLE I-continued

```
(40)
AAT CCA GAT TGG GAC TTC AAC CCC ATC AAG GAC CAC TGG CCA
Asn Pro Asp Trp Asp Phe Asn Pro Ile Lys Asp His Trp Pro (54)
GCA GCC AAC CAG GTA GGA GTG GGA GCA TTC GGG CCA GGG CTC
Ala Ala Asn Gln Val Gly Val Gly Ala Phe Gly Pro Gly Leu (68)
ACC CCT CCA CAC GGC GGT ATT TTG GGG TGG AGC CCT CAG GCT
Thr Pro Pro His Gly Gly Ile Leu Gly Trp Ser Pro Gln Ala (82)
CAG GGC ATA TTG ACC ACA GTG TCA ACA ATT CCT CCT CCT GCC
Gln Gly Ile Leu Thr Thr Val Ser Thr Ile Pro Pro Pro Ala (96)
TCC ACC AAT CGG CAG TCA GGA AGG CAG CCT ACT CCC ATC TCT
Ser Thr Asn Arg Gln Ser Gly Arg Gln Pro Thr Pro Ile Ser (110)                             (119)
CCA CCT CTA AGA GAC AGT CAT CCT CAG GCC
Pro Pro Leu Arg Asp Ser His Pro Gln Ala
```

PRE-S2 REGION

```
(120)
ATG CAG TGG AAT TCC ACT GCC TTC CAC CAA GCT CTG CAG GAT
Met Gln Trp Asn Ser Thr Ala Phe His Gln Ala Leu Gln Asp (134)
CCC AGA GTC AGG GGT CTG TAT TTT CCT GCT GGT GGC TCC AGT
Pro Arg Val Arg Gly Leu Tyr Phe Pro Ala Gly Gly Ser Ser (148)
TCA GGA ACA GTA AAC CCT GCT CCG AAT ATT GCC TCT CAC ATA
Ser Gly Thr Val Asn Pro Ala Pro Asn Ile Ala Ser His Ile (162)                                    (174)
TCG TCA AGC TCC GCG AGG ACT GGG GAC CCT GTG ACG AAC
Ser Ser Ser Ser Ala Arg Thr Gly Asp Pro Val Thr Asn
```

S PROTEIN

```
ATG GAG AAC ATC ACA TCA GGA TTC CTA GGA CCC CTG CTC GTG
Met Glu Asn Ile Thr Ser Gly Phe Leu Gly Pro Leu Leu Val

TTA CAG GCG GGG TTT TTC TTG TTG ACA AGA ATC CTC ACA ATA
Leu Gln Ala Gly Phe Phe Leu Leu Thr Arg Ile Leu Thr Ile

CCG CAG AGT CTA GAC TCG TGG TGG ACT TCT CTC AAT TTT CTA
Pro Gln Ser Leu Asp Ser Trp Trp Thr Ser Leu Asn Phe Leu

GGG GGA TCA CCC GTG TGT CTT GGC CAA AAT TCG CAG TCC CCA
Gly Gly Ser Pro Val Cys Leu Gly Gln Asn Ser Gln Ser Pro

ACC TCC AAT CAC TCA CCA ACC TCC TGT CCT CCA ATT TGT CCT
Thr Ser Asn His Ser Pro Thr Ser Cys Pro Pro Ile Cys Pro

GGT TAT CGC TGG ATG TGT CTG CGG CGT TTT ATC ATA TTC CTC
Gly Tyr Arg Trp Met Cys Leu Arg Arg Phe Ile Ile Phe Leu

TTC ATC CTG CTG CTA TGC CTC ATC TTC TTA TTG GTT CTT CTG
Phe Ile Leu Leu Leu Cys Leu Ile Phe Leu Leu Val Leu Leu

GAT TAT CAA GGT ATG TTG CCC GTT TGT CCT CTA ATT CCA GGA
Asp Tyr Gln Gly Met Leu Pro Val Cys Pro Leu Ile Pro Gly

TCA ACA ACA ACC AAT ACG GGA CCA TGC AAA ACC TGC ACG ACT
Ser Thr Thr Thr Asn Thr Gly Pro Cys Lys Thr Cys Thr Thr

CCT GCT CAA GGC AAC TCT ATG TTT CCC TCA TGT TGC TGT ACA
Pro Ala Gln Gly Asn Ser Met Phe Pro Ser Cys Cys Cys Thr

AAA CCT ACG GAT GGA AAT TGC ACC TGT ATT CCC ATC CCA TCG
Lys Pro Thr Asp Gly Asn Cys Thr Cys Ile Pro Ile Pro Ser

TCC TGG GCT TTC GCA AAA TAC CTA TGG GAG TGG GCC TCA GTC
Ser Trp Ala Phe Ala Lys Tyr Leu Trp Glu Trp Ala Ser Val
```

TABLE I-continued

```
CGT TTC TCT TGG CTC AGT TTA CTA GTG CCA TTT GTT CAG TGG
Arg Phe Ser Trp Leu Ser Leu Leu Val Pro Phe Val Gln Trp

TTC GTA GGG CTT TCC CCC ACT GTT TGG CTT TCA GCT ATA TGG
Phe Val Gly Leu Ser Pro Thr Val Trp Leu Ser Ala Ile Trp

ATG ATG TGG TAT TGG GGG CCA AGT CTG TAC AGC ATC GTG AGT
Met Met Trp Tyr Trp Gly Pro Ser Leu Tyr Ser Ile Val Ser

CCC TTT ATA CCG CTG TTA CCA ATT TTC TTT TGT CTC TGG GTA
Pro Phe Ile Pro Leu Leu Pro Ile Phe Phe Cys Leu Trp Val

TAC ATT TAA
Tyr Ile
```

Additionally the following terms used throughout the specification are defined as follows:

An "expression cassette" is defined as any discrete region of DNA which functions in yeast as a complete gene expression unit.

A "complete gene expression unit" is a structural gene and the promoter and regulatory regions required for its transcription and translation.

A "functional DNA coding region" means a DNA coding sequence which, when fused in phase to the S protein coding sequence, does not interfere with the assembly of the HBsAg mixed particle.

A "functional derivative" means a coding sequence having amino acid alterations which do not interfere with particle formation and which retain immunogenicity or other functionality. Such functional derivatives can be prepared by conventional site specific mutagenesis [See, e.g., Botstein et al, Science, 229:1193 (1985)] or by other standard techniques.

A "vector" is defined as DNA which can carry and maintain the DNA fragment of the invention, including, for example, phages and plasmids. These terms are understood by those of skill in the art of genetic engineering.

The method of this invention involves coexpressing in a yeast cell a first protein S and a second protein X-S, where S is substantially the major surface protein of HBV and where X is encoded by a functional DNA coding region fused in phase to the S coding sequence and X is either preS1S2 or preS2, or one or more other immunologically important polypeptides, or a functional derivative thereof. The method of this invention may also involve optional third, fourth and other proteins of the formula Y-S, where Y is defined identically to X but is different from X.

According to the invention, the HBsAg antigen S protein is coexpressed with the X or Y amino acid sequence, with the X or Y sequence being in the form of a fusion protein with S. The coding regions of the selected X or Y, as well as the sequence for the S protein may be selected from published sequences and constructed by conventional chemical or recombinant DNA techniques.

Preferred functional DNA coding regions for X and/or Y include, but are not limited to, the entire HBV preS protein coding sequence, or an immunogenic derivative thereof, e.g., the preS2, preS or preS1S2 protein coding sequence, or immunogenic derivatives thereof. L proteins when incorporated into the mixed particles of this invention, produce a particle comprising S proteins and proteins having the important CTL epitopes from the preS region of the L protein.

Certain S, or preS sequences are published and may include those sequences disclosed in copending U.S. patent application Ser. No. 009,325 incorporated herein by reference, as well as the sequences provided in Table I.

Other X and/or Y fusion components include other immunogenic coding sequences such as coding sequences from the HBV core protein or the coding sequence of the repeat region of the circumsporozoite protein of Plasmodium, or an immunogenic derivative thereof [see, e.g., published application PCT/BE88/00002]; an HIV protein or an immunogenic derivative thereof, such as, all or part of the coding sequences for the HIV envelope proteins gp160 and gp120; an influenza virus protein or an immunogenic derivative thereof, such as proteins derived from the HA2 subunit of the HA protein, such as the "C13" and "D" proteins disclosed in copending application U.S. Ser. No. 07/238,801, which is incorporated herein by reference.. Such sequences are published and known to those of skill in the art.

Alternatively, X or Y or additional fusion coding sequences used in this method may each be an immunologically important epitope(s), or part of a protein selected from any pathogenic microorganism, virus, or cell of interest. Such epitope or part of a protein may function to induce an antibody response, a $T_h$ (helper T cell) response, or may function as a $T_c$ (cytotoxic T cell) epitope and thereby function to induce a CTL response which has been shown to be important in immunoprotection against several infectious disease states.

Alternatively, X or Y can comprise a functional domain of a biologically active- enzyme or other protein. The method of the present invention is not limited to the particular component of X or Y, nor to the number of X-S and Y-S type proteins employed in the co-expression.

According to this method S is preferably the entire mature surface protein (about 226 amino acids) of HBV (see Table I). In the protein fusions used in the method of this invention, e.g., X-S, S means a protein encoded by an S protein coding sequence of the HBV genome, wherein S is substantially the same as an authentic HBsAg S protein. Truncates of S can also be employed in this method as long as particle assembly is not adversely affected.

It now appears that there are epitopes within the pre-S region of the L protein which are important in inducing a cytotoxic T cell (CTL) response. However, particles consisting of L protein are difficult to produce. However the L proteins may be employed in the mixed particles of this invention. This invention thereby provides a means to produce a particle comprising S proteins and L proteins having the important CTL epitopes from the pre-S region.

The HBsAg S protein coding sequence can be isolated from DNA extracted from Dane particles in infected human serum by filling in the single strand region with a DNA polymerase, preferably the endogenous polymerase, followed by digestion with a restriction endonuclease. The choice of endonuclease will depend, in part, on the particular Dane particles. For example, the HBsAg coding sequence of HBV DNA of certain Dane particles of the adw serotype can be isolated on a single BamHI fragment; the HBsAg coding sequence of HBV DNA of certain Dane particles of the ayw serotype can be isolated on a HhaI fragment. HBV DNA of Dane particles of the same serotype may also exhibit different patterns of restriction sites.

Once isolated as described above, the S protein coding sequence is employed in the coexpression method of the present invention in two ways. First the S protein coding sequence is placed into a vector or an expression cassette employing conventional techniques to allow expression of the S protein in the yeast host. Secondly, the S protein coding sequence or a substantial portion thereof is employed in the fusion protein with X or Y, or any other additional epitope.

Fusing of the HBsAg S sequence to the polypeptides X or Y can be accomplished by use of intermediate vectors. Alternatively, the HBsAg S sequence can be inserted directly into a vector which contains the X or Y polypeptide coding region. Techniques for cloning DNA fragments in phages are disclosed, for example, by Charnay et al, *Nature*, 286:893–895 (1980) and Tiollais, United Kingdom Patent Application 2,034,323.

Thus, the protein X-S, for example, is constructed in a vector comprising a DNA molecule operatively linked to a regulatory region. The DNA molecule contains the functional DNA coding sequence X fused in the proper reading frame to the HBsAg protein S. This DNA molecule or an expression cassette containing the X coding sequence, which may be any functional DNA coding sequence of interest, fused in frame to a portion of the S protein coding sequence can be constructed by conventional techniques, such as by ligating the X coding sequence in the appropriate reading frame to any codon within the S protein coding region.

Such fusion may occur at the N-terminus of the S protein coding sequence or at some-point within the S protein. The fusion may occur at the 5' terminus of the preS2 region, or at some point within the preS2 region so that preS2 DNA flanks both sides of the functional DNA coding sequence, or at the 5' terminus of a truncated portion of the preS2 region, or at the 5' terminus of the S protein coding region. Preferably, enough of the S coding sequence remains after ligation of the X coding sequence, especially where X represents a B epitope-of interest, to insure optimal presentation of the X protein on the resulting HBsAg particle surface. Where X represents a T cell coding sequence, enough of the S coding sequence should remain after, ligation of the X coding sequence to ensure particle formation. The construction of the fusion proteins may also be prepared according to methods described in copending U.S. patent application Ser. No. 009,325, incorporated herein by reference.

Restriction of DNA to prepare DNA fragments used in the invention, ligation of such fragments to prepare recombinant DNA molecules used in the invention and insertion into microorganisms are carried out by known techniques such as techniques disclosed in the previously and subsequently cited references. Conditions are selected to avoid denaturation of the DNA and enzymes. Restriction enzymes and ligases used in carrying out this invention are commercially available and should be used in accordance with instructions included therewith. T4 DNA ligase is the preferred ligase.

The various fragments and final constructions used for the coexpression of the S protein, the X-S and, Y-S fusion proteins, and the components of the vectors carrying these coding sequences for coexpression into yeast cells in the method of the present invention may be joined together using with conventional methods known to those of skill in the art. In many cases, genes have been isolated and restriction mapped, as well as sequenced. To that extent, one can select the sequence of interest, such as the HBsAg sequence, by restriction of the gene, employing further manipulation as necessary such as resection with Bal31 in vitro mutagenesis, primer repair, or the like, to provide a fragment of a desired size, including the desired sequence, and having the appropriate termini. Linkers and adapters can be used for joining sequences, as well as replacing lost sequences, where a restriction site employed was internal to the region of interest. The various fragments which are isolated, may be purified by electrophoresis, electroeluted, ligated to other sequences, cloned, reisolated and further manipulated.

The use of regulatory regions for controlling transcription of the structural gene of interest, such as the HBsAg sequence S and the X-S sequence, e.g., the M protein of HBsAg, may allow for growing the host cells to high density with no or low levels of expression of the structural gene, and then inducing expression by changing the environmental conditions, such as nutrient, temperature, and the like.

The vector carrying the S protein coding sequence and the one or more vectors carrying the X-S, Y-S or other fusion proteins of that formula are coexpressed into a yeast host cell by conventional techniques. The cell is then cultured in appropriate culture media, i.e., media which enables the host to express the S protein and X-S and Y-S fusion proteins in mixed particles in recoverable quantity. One exemplary medium for such use is Yeast Nitrogen Base (YNB) minimal medium. The appropriate culture media may be selected by one of skill in the art depending upon the particular host employed in the method.

Resulting hybrid X-S and Y-S proteins will be produced simultaneously in yeast cells and assembled as mixed particles together with the S protein. Such mixed particles are herein defined as a multimeric assembly of two or more polypeptides into a particulate structure, which is therefore characterized by a composite nature. At the surface of the mixed particles the different peptides are disposed in different spatial association. The method of the present invention thus allows the formation of conformational epitopes of pathogenic microorganisms at the surface of an HBsAg mixed particle.

Where X and Y are components of a conformational determinant, the method enables spatial assembly of the amino acid sequences, e.g. X-S and Y-S, in such a manner that the presence of X and Y on the HBsAg particle will elicit an immune response similar to that associated with recognition of the native determinant. For example, the components X and Y may comprise the preS2 and/or preS1 protein of HBsAg. When employed as fusions to S, mixed particles are produced. The present invention thereby enables the production of HBsAg particles in yeast which mimic natural particles based on their content of the S, M and/or L proteins of HBV.

The isolation of the mixed particle of the invention from a cell lysate or extract of the culture medium is performed by conventional protein isolation techniques.

A preferred embodiment of the method according to the present invention employs Ty integrative vectors for co-expression of the fused proteins in the yeast cell. Ty elements are a family of naturally occurring transposable elements from the yeast *Saccharomyces cerevisiae* that are structurally similar to retroviral proviruses and the copia element family of Drosophila. Such Ty elements and examples of vector systems are described in detail in Mellor et al, *Yeast*, 2:145 (1986); Boeke et al, *Cell*, 40:491 (1985); Boeke et al, *Cell*, 42:507 (1985) and copending U.S. patent applications Ser. Nos. 101,463 and 233,631 [SKB 12083 and 12083-1], which applications and references are incorporated herein by reference. Preferably the Ty based plasmids and linear vectors are derivatives of the Ty1 element isolated from the CAR1 locus of the strain cargA$^+$O$^h$-1 [Jauniaux et al, *EMBO J.*, 1:1125 (1982)] and plasmid YEP URA3$^+$ cargA$^+$O$^h$-1.

Ty elements may be isolated from strains of *S. cerevisiae* by standard techniques known to those of skill in the art. Numerous strains of *S. cerevisiae* are available from public depositories and laboratories, e.g., American Type Culture Collection, Rockville, Md. (ATCC). The Ty elements are approximately 5.9 kb in length with terminally repeated delta sequences or direct LTRs of approximately 335 bp surrounding the internal region of 5.3 kb. Two classes of Ty elements may be employed in the present invention, Ty1 and Ty2, which differ essentially by two large internal substitutions.

Construction of Ty vectors for use in carrying the S protein and the X-S and/or Y-S fusions of the present invention allow these sequences to be stably integrated into the chromosomes of the yeast host cell. Such integrations are stable due to their low frequency of excision. The vectors are thus homogeneously distributed in the cell population, allowing a similar rate of protein synthesis in each cell. The Ty vectors ensure that the relative copy number of the integrated copies can be controlled and can remain the same in each cell. Use of the Ty vectors permits the production of substantially homogenous mixed particles according to this embodiment of the invention. The method thus allows the yeast cell to produce two or more gene products in the same strain at well defined levels and with the same efficiency in each cell of the population.

The use of this Ty vector expression system according to the method of the invention is exemplified as follows. Two independently different expression cassettes may be introduced into the same yeast host strain and stably integrated into the chromosomes. One Ty1 vector contains, e.g. the URA3 marker and contains the TDH3-HBsAg (S antigen)-ARG3 cassette described in Example 1, containing a strong glycolytic promoter allowing constitutive expression of the S antigen. The other vector is introduced into the same yeast strain carrying the LEU2 or TRP1 marker with a preS-S expression cassette (preS2S or preS1S2S), e.g., as described in U.S. patent application Ser. No. 009,325.

Promoters useful for expressing the preS-S cassettes include ARG3 or other promoters which allow modulation of the level of the preS-S antigen relative to the S antigen depending on the composition of the growth medium. In the case of ARG3, media containing arginine or no arginine allow different expression levels. Transformants, growing on different media, can synthesize and assemble the mixed particles of the invention having various compositions.

Ty sequences can be used to direct integration of vectors into the chromosomes of a yeast host cell by standard homologous recombination with resident Ty1 elements. More than ten Ty1 copies are present in the chromosomes of most conventionally used *S. cerevisiae* laboratory strains. According to the method employing Ty vectors for homologous recombination, different haploid yeast strains are transformed independently with the different vectors. These strains can have the same or different mating type. The transformants are easily characterized by stability of the vector, copy numbers and expression levels. Haploid transformants having different vector copy numbers and different expression levels can be chosen and different diploid strains can be constructed. In such diploid strains different relative copy numbers of the two or more vectors can be obtained.

Copy numbers can also be increased by classical. genetics using series of haploid transformants carrying integrated vectors at different Ty loci. Also, the *S. cerevisiae* CUP1 metallothionein structural gene which allows resistance to copper can be used in Ty vectors with CUP$_S$ or cup1▲ recipient strains (to avoid amplification of CUP1 genes at the CUP1 locus) and allow the monitoring of vector copy numbers. Such cup1▲ strains have been obtained previously, as described, for example in D. H. Hamen et al, *Science*, 228:685 (1985).

Other *S. cerevisiae* genes which may be used as marker genes for selection of Ty vector integrations in the same host strain are the following: URA3, TRP1, LEU2, and ARG3. Still other marker genes in other yeast species may also be used in an analogous method to construct integrative vectors according to the present invention. These two Ty1 based vector systems can be used to obtain strains of *S. cerevisiae* synthesizing two or more different polypeptides susceptible to association in vivo or during extraction to form the hybrid particles.

Other integratable vectors may also be employed in this method, including, for example, the Ty2 element, in a manner analogous to the use of the Ty1 element described above and in the examples. Additionally, retrotransposition vectors described in U.S. patent application Ser. No. 07/233, 631, incorporated herein by reference, may also be designed. Additionally, other genomic repetitive DNA sequences may be employed in a manner analogous to the employment of the Ty sequences. For example, single Ty LTR sequences may also be used to assist in the stable integration of the S, X-S and Y-S fusion protein coding sequences into the chromosome of a yeast strain, as well as any other repetitive genomic DNA sequences, e.g., the Ty delta sequence. [See, e.g., Z. Jingdong, "Heterologous Gene Expression in *Saccharomyces cerevisiae* Using a Dominant Selection and Amplification System", thesis from the University of Ghent, Belgium (1986–87)].

In other yeast genera no Ty sequences are present and therefore vector systems must be designed to provide coexpression of the S, X-S and Y-S protein coding sequences in yeast to create the mixed particles described. Therefore, expression cassettes may be designed for easy integration into the yeast chromosomes employing other repetitive DNA sequences or plasmids such as ARS based plasmids in yeast such as Pichia, allowing integration into the chromosomes. An example of such applicable ARS plasmids is described in Cregg et al, *Mol. Cell. Biol.*, 5(12):3376 (1985). In the expression systems described above, e.g. both the Ty expression systems and others, the regulatory element comprises a promoter which effects RNA polymerase binding and transcription. Regulatable, i.e., inducible or derepressible, promoters, can also be used. A variety of useful promoters are available for expression of heterologous polypeptides in yeast. These include the copper inducible metallothionein gene (CUP1) promoter and the constitutive promoter of the glycolytic genes, glyceraldehyde-3-phosphate dehydrogenase (TDH3) and alcohol dehydrogenase (ADH). Regions for transcription termination in yeast are derived from the 3' end of any of several yeast genes, for example, the gene for iso-1-cytochrome C (CYC1). Expression systems for use in Kluyveromyces are disclosed, e.g., in PCT WO83/04050, Hollenberg et al; in Schizosaccharomyces, e.g., in EP-A-107170, Yamomoto; in Pichia, e.g., in Cregg et al, *Bio/Technology,* 5:479 (1987); and in Hansenula, e.g., in EP-A-299108, Hollenberg et al.

Thus, any known promoter capable of controlling the expression of the fusion protein coding sequences in yeast may be selected. For example, PGK, TDH3, ARG3, and APH1 are illustrative promoters useful in the vectors of the present invention. However, if regulatable promoters are chosen, for example, PHO5, GAL1, and CUP1, protein synthesis must be induced in such a way that the different constituents of the particles will be produced in well defined relative amounts. One way to control these relative expression levels of the different proteins is to use two or more promoters having different strengths. For example, strong promoters such as TDH3 could be used to control the expression for abundant proteins, and less efficient promoters such as ARG3 could be used to control the expression of minor proteins when coexpressed in yeast to produce the particles of the invention.

In the practice of the methods of this invention, any species of yeast host for which transformation, cloning and expression systems are available may be employed in developing "mixed particles" of HBsAg. The examples below employ Saccharomyces, specifically *S. cerevisiae.* However, other yeast species may be employed including, without limitation, Hansenula, Pichia, Candida, Kluyveromyces and Schizosaccharomyces.

Specifically provided by the examples of this invention is an *S. cerevisiae* strain containing two or more Ty vectors capable of synthesizing simultaneously different HBsAg molecules and forming mixed HBsAg particles in vivo in such strains or during extraction. For example, the method of the invention using Ty1 based integrative vectors in Examples 1–4, allows variation of the copy numbers of three expression cassettes and, consequently, the relative expression levels of the three envelope proteins of HBsAg. Individual expression of S or M protein in yeast leads to recovery of these proteins in particles similar to the 22 nm particles present in serum of HBV patients. Thus, the mixed (S,M) lipoprotein structures detected upon simultaneous expression of the S and M protein are likely true particles. Mixed particles were only found when the different surface proteins are expressed in the same cell. Simultaneous cell rupture and subsequent processing of two strains producing different surface proteins (mixture of cells from independent cultures) does not give rise to mixed structures.

Preferred yeast strains are devoid of functional chromosomal CUP1 genes, which are sensitive to copper toxicity, in order to readily select transformants having integrated several copies of vectors. Two preferred cup1▲ yeast strains are described below in Example 9.

The method of the present invention for producing such mixed particles has advantageous utility in the production of vaccines to pathogenic microorganisms. For example, the mixed HBsAg particle described in the examples may be constructed to resemble particles or filaments or virions present in the blood of a patient that contain preS2 and preS1 epitopes exposed at their surface in addition to epitopes from the major proteins. These particles therefore may be useful in various formulations for an HBV vaccine. In the formation of these vaccines only a fraction of the envelope proteins present in the particles must be M or L proteins in order to avoid the masquage of epitopes present on the major proteins. Mixed particles may have immunogenic properties that are not obtained with individual mixtures of S, M and L proteins.

Further, because purification of L particles is difficult and has not been reported with accuracy, the method of the present invention provides a method for producing particles carrying the entire preS1S2 region.

The method of the present invention also allows the formation of conformational epitopes using mixed hybrid particles of other than HBsAg origin. For example, the malarial circumsporozoite protein, particularly the repeat region, or various proteins of HIV virus such as fragments of gp160 or gp120 and other proteins from various microorganisms, viruses or cells may be employed in the method according to the present invention. These multimeric structures may also be employed as vaccine components for the appropriate diseases.

For example, the method of the invention allows the formation of mixed hybrid particles carrying both B-cell epitopes and the relevant T-helper epitopes to enhance the B-cell response against a pathogen of interest. [See, e.g., Milich et al, *Nature,* 329:547 (1987).] The method of the invention also allows the formation of mixed hybrid particles carrying cytotoxic T cell epitopes to induce a protective cellular immune response against a pathogen of interest. Mixed hybrid particles may be an efficient delivery system to elicit T-cell responses [See, e.g., Yiu et al, *J. Exp. Med.,* 168:293 (1988)]. The method of the invention also allows the formation of mixed hybrid particles carrying any combination of B, $T_H$ and $T_C$ epitopes to induce both a humoral and cellular immune response to the pathogen of interest.

Thus this invention encompasses vaccines containing the mixed particles of the invention. Such vaccine will contain an immunoprotective quantity of the mixed particles, i.e., enough of the particles are administered to elicit sufficient protective antibody response against the agent desired to be protected against without serious side effects. Such vaccines may be prepared by conventional techniques. For example, a vaccine for stimulating protection against HBV infection in humans may contain the mixed particle described above and a suitable conventional carrier. The mixed particle may be in an aqueous solution buffered at physiological pH for direct use. Alternatively, the particle can be admixed or adsorbed with a conventional adjuvant, such as; aluminum hydroxide or aluminum phosphate. Such a mixed particle may also be combined with other immunogens to prepare combination vaccines. See, e.g., New Trends and Developments in Vaccines, eds. Voller et al, University Park Press, Baltimore, Md. (1978).

Such vaccines can be administered by an appropriate route, e.g., by the subcutaneous, intravenous or intramuscular routes. The amount of the mixed particle of the invention present in each vaccine dose is selected by the attending physician with regard to consideration of the patient's age, weight, sex, general physical condition and the like. The amount to induce an immunoprotective response in the patient without significant adverse side effects may vary depending upon the immunogen employed and the optional presence of an adjuvant. Generally, it is expected that each dose will comprise 1–1000 micrograms of protein, preferably 1–200 micrograms. Initial doses may be optionally followed by repeated boosts, where desirable.

Another use for the mixed particles of this invention may be as probes or reagents for detection of HBV or other pathogenic organisms in biological samples by various conventional immunoassays and the like.

The following Examples 1–4 illustrate the method of the invention in the construction of a yeast strain carrying HBsAg expression cassettes encoding respectively the S and M, the S and L, or the three surface proteins integrated in their genomes. Such strains synthesize simultaneously different surface proteins. The presence of (S,M), (S,L) or (S,M,L) mixed lipoprotein structures in yeast extracts is also demonstrated by immuneprecipitation of the major protein with monoclonal antibodies that are specific for the middle and the large proteins. Examples 5–8 demonstrate immunogenicity testing of the particles and other applications of the methods of the present invention. Example 9 describes certain preferred yeast strains for production of the particles of this invention.

EXAMPLE 1

Ty Integrative Vectors Carrying HBsAg Expression Cassettes

The Ty vectors containing expression cassettes and selective markers are constructed as follows. Expression cassettes for HBsAg proteins were designed by linking DNA sequences encoding the major (S), middle (M) or large (L) envelope proteins to the TDH3 (glyceraldehyde 3 phosphate dehydrogenase) sequences upstream from the ATG (including the TDH3 promoter sequences) and to the ARG3 transcriptional terminator forming vectors pRIT12363(S), pRIT12660(M) and pRIT12845(L), substantially as described in Rutgers et al, (1988) cited above, which is incorporated herein by reference.

pRIT12363 contains a 2900 base pair (bp) expression cassette consisting of a HBV DNA derived coding sequence for the 226 amino acids of the S protein flanked 5' by, and under the control of, a 1050 bp TDH3 promoter fragment and 3' by a 1150 bp fragment carrying the ARG3 transcription terminator [Harford et al, *Post. Grad. Med. J.*, 63:Suppl. 2, 65–70 (1987)].

pRIT12660 contains a 3050 bp expression cassette consisting of a HBV DNA derived coding sequence for the 281 amino acids of the M protein flanked 5' by, and under the control of, a 1050 bp TDH3 promoter fragment and 3' by a 1150 bp fragment carrying the ARG3 transcription terminator.

pRIT12845 contains a 3370 bp expression cassette consisting of a HBV DNA derived coding sequence for the 389 amino acids of the L protein flanked 5' by, and under the control of, a 1050 bp TDH3 promoter fragment and 3' by a 1150 bp fragment carrying the ARG3 transcription terminator.

Co-owned copending U.S. patent application Ser. No. 009,325 is also incorporated by reference for description of these vectors, and sequences of preS1 and preS2. However, these particular vectors and expression cassettes are merely exemplary and not essential to the practice of the present invention.

Figure 1:
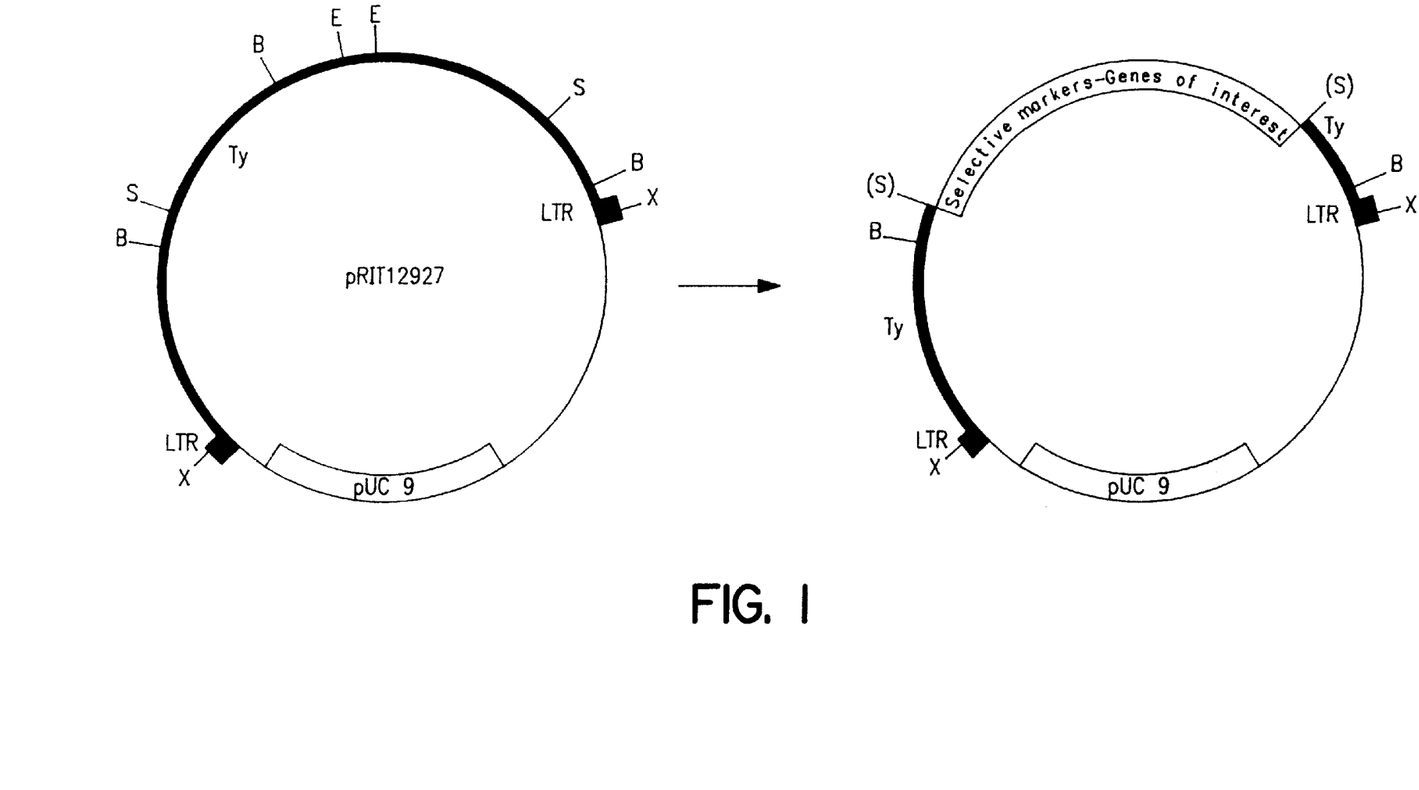
Figure 2:
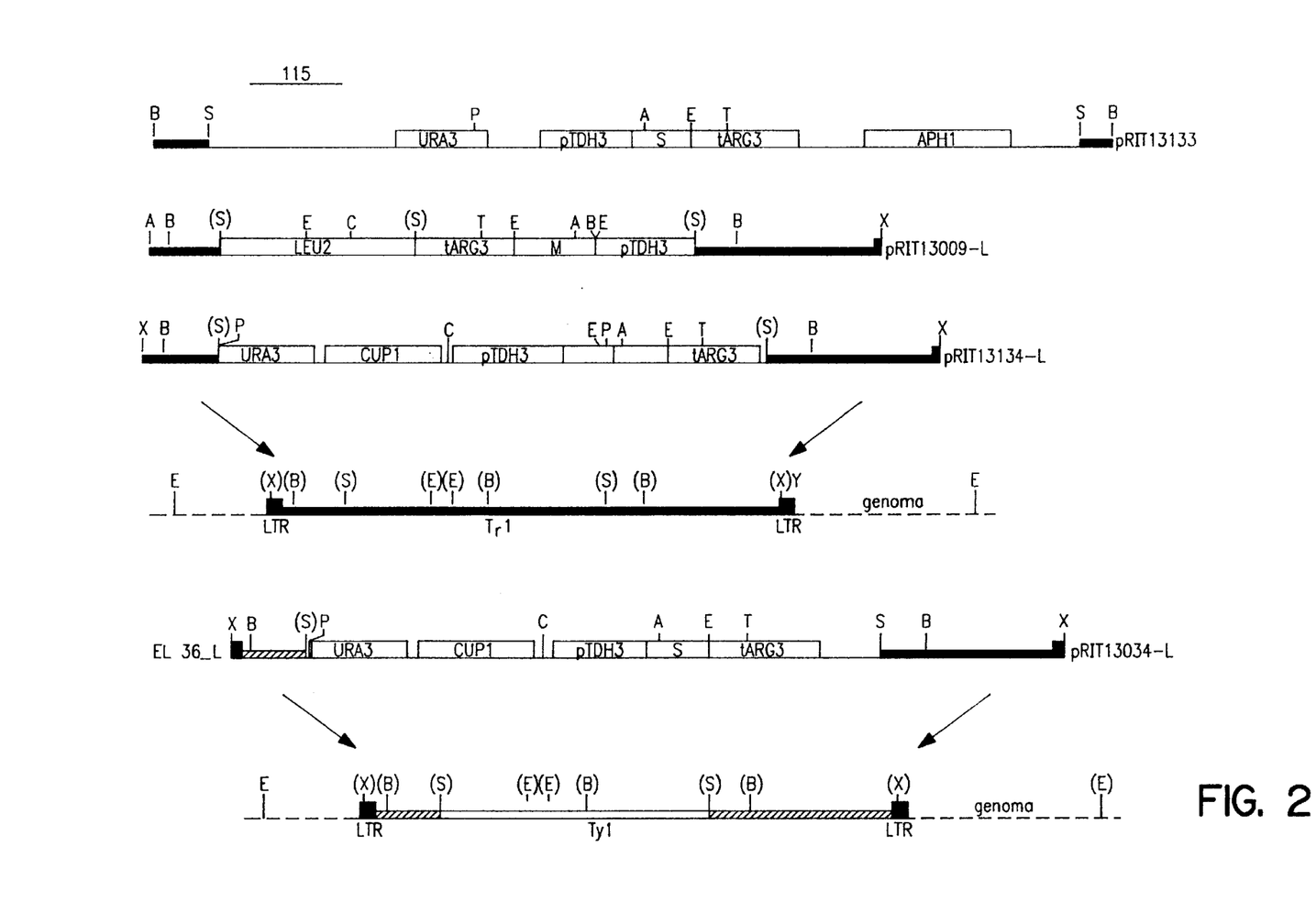
FIG. 2 is a schematic illustrating the expression cassettes of pRIT13133-L, pRIT13009-L, pRIT13134-L and pRIT13034-L inserted into the constructs of FIG. 1, in association with appropriate selection markers. XhoI or BglII DNA fragments having Ty homology at both ends are purified for transformation of appropriate S. cerevisiae host strains. Additional restriction sites are P for PstI, A for XbaI, T for SacII, C for ClaI. pRIT13034-L is identical to pRIT13134-L, except that it contains an S expression cassette, instead of the L cassette. The S expression cassette is a ClaI-SalI DNA fragment isolated from pRIT12353, which is identical to pRIT12363 with an additional 547 base pair segment from pBR327 after the ARG3 terminator.

The Ty based plasmids and linear vectors are derivatives of the Ty1 element isolated from the CAR1 locus of the plasmid strain YEP URA3$^+$ cargA$^+$O$^h$-1 [Jauniaux et al, (1982) cited above]. The HindIII fragment containing this Ty1 element and adjacent CAR1 sequences was cloned in the SalI site of pUC9 [Amersham, U.K.; Pharmacea, Sweden] after T4 polymerase treatments, giving rise to plasmid pRIT12927 (see FIG. 1A). All Ty1 based vectors described herein are derivatives of pRIT12927 in which the heterologous DNA sequences of interest replace the Ty1 internal SalI fragment (see FIG. 1B). Linear vectors are either BglII or XhoI DNA fragments purified from the Ty plasmids after electrophoresis on 0.8% agarose gels. These vectors can be integrated into the genome by homologous recombinations with resident Ty1 elements. URA3 or LEU2 genes were used as markers for selection of the transformants through complementation of the ura3 or leu2 mutation.

A. Vector pRIT13133-L

To form this vector, the SalI fragment inserted in Ty1 is a derivative of pBR322 containing the *S. cerevisiae* URA3 gene, the APH1 (Km$^r$) gene from Tn903 and the HBsAg cassette pTDH3-S-tARG3 [See FIG. 1B]. The APH1 gene from Tn903 which is present on the vector pRIT13133-L is expressed in *S. cerevisiae*, conferring G418 resistance [Jimenez et al, *Nature*, 287:869 (1980)], and can be used as an additional selective marker. The APH1 gene was inserted as a 1.7 PvuII fragment [Grindley et al, *Proc. Natl. Acad. Sci. USA*, 77:7176 (1980)] in the HINDIII site of pBR322 after T4 polymerase treatments. The URA3 gene from vector YIP5 [Struhl et al, *Mol. Gen. Genet.*, 176:335 (1979)] is inserted in pBR322 by replacement of the BglI fragment (pBR322, 1169–3488) after T4 polymerase treatments. The expression cassette for the S protein from plasmid pRIT12363, described above, was inserted in the PstI site of pBR322 as a HindIII fragment after T4 polymerase treatments to produce pRIT13133L.

B. Plasmid pRIT13133

In the plasmid pRIT13133, the DNA sequences inserted in Ty1 are the same as in the vector pRIT13133-L. Ty sequences extend to the LTR XhoI sites and were ligated at XhoI.

C. Vector pRIT13009-L

The LEU2 gene was inserted in the SalI site of Ty1 as a SalI-XhoI fragment isolated from the vector pCV9 [Petes, *Cell*, 19:765 (1980)]. The expression cassette for the M protein from plasmid pRIT12660, described above, was subsequently inserted in the remaining SalI site as a HindIII fragment after T4 polymerase treatments.

D. Vector pRIT13134-L

URA3 gene [Rose et al, *Gene*, 29:113 (1984)] is carried on a BglII fragment from plasmid pFL44 [Laboratoire de Genetique Physiologique—C.N.R.S. Strasbourg]. The CUP1 gene is a XbaI-KpnI DNA fragment [Butt et al, *Proc. Natl. Acad. Sci.*, 81:3332 (1984); Fogel et al, *Curr. Genet.*, 7:347 (1983)]. The CUP1 gene present on the vector pRIT13136-L is an additional marker that can be used in CUP1$^s$ or cup1▲ recipient strains. The expression cassette for the L protein is a HindIII fragment from plasmid pRIT12845, described above. These DNA fragments were inserted in Ty1 in a multistep construction and are joined by DNA linkers.

EXAMPLE 2

Integration of Vectors Carrying HBsAg Expression Cassettes in the Chromosomes of *S. cerevisiae*

*S. cerevisiae* strain 10S69d (ura3 Leu2 Trp1 gall, α) [Vrije Universiteit Brussels] and the isogenic strain of opposite mating type (10S69d a), obtained by mating type switching using a 2μ plasmid carrying the HO gene [Cold Spring Harbor Laboratory] were transformed with the linearized recombinant Ty vectors described in Example 1. The linear Ty vectors (BglII or XhoI DNA fragments) were purified after digestion of parent plasmids followed by electrophoresis through 0.8% agarose gels. Samples containing 0.2 to 2 μg of such DNA fragments and approximately 20 μg of sonicated salmon sperm DNA were used to transform approximately $10^8$ cells (spheroplasts), following the method of Hinnen et al, *Proc. Natl. Acad. Sci.*, 75:1929 (1978). Strains are cultivated on YNB minimal medium with 2% glucose as carbon source. Tryptophan and leucine were supplemented at 100 μg/ml.

A series of URA3 transformants were obtained and purified. The URA3 gene is used in these transformations for selection of URA$^+$ colonies (complementation of the ura3$^-$ mutation). One copy of the URA3 gene is sufficient to allow the cell growth in the absence of uracil in the medium. The majority of these transformants are relatively stable. Reversion frequency to ura3 is lower than $10^{-4}$ after about 10 generations of growth on YEPD non-selective medium consisting of 1% yeast extract, 2% bactopeptone and 2% glucose.

Integration events were analyzed by Southern blot. Yeast DNA isolation was performed as described by Davis et al, *Meth. Enzymol.*, 65:404 (1980). Southern blot analyses were performed as described by Maniatis et al, "Molecular Cloning, A Laboratory Manual", Cold Spring Harbor Laboratory, Cold Spring Harbor, N.Y. (1982). Total DNA was prepared from series of candidates, digested with EcoRI and after electrophoresis on agarose gels, transferred to nitrocellulose filters. An HBV specific DNA probe, the nick translated EcoRI-XbaI DNA fragment from the region coding for the major (S) protein, was used for the detection of EcoRI genomic DNA fragments carrying the expression cassette. Since there is only one EcoRI site on the vector, each band corresponded to one vector copy. One to several copies of vector can be integrated in the transformants. One particular band present in a number of strains, varied in intensity. Its size was compatible with the occurrence of perfect tandem arrays of vectors. The plasmid pRIT13133 linearized with EcoRI has the size expected for tandem EcoRI fragments of integrated pRIT13133-L vector. It migrated identically to the putative tandem fragment observed on Southern blots.

A series of transformants were crossed with the strain 10S69d (a), and 2/2 segregations of the URA3 marker were observed, as well as 2/2 segregation of the EcoRI genomic fragments detected with the HBsAg DNA probe. This showed that multiple integration events were obtained at a single Ty locus. However, some of these genomic fragments can be sometimes lost after meiosis. A series of transformants were characterized, each carrying several vector copies at one particular Ty locus.

Because many strains contain several copies of vector integrated at single loci including frequently two or three genomic EcoRI fragments homologous to the HBV probe in addition to the putative tandem fragment, other arrangements of vectors may occur in addition to tandem repeats.

Strains containing one to several copies of the expression cassettes encoding the M or L proteins were obtained and characterized in a similar way, using the vectors pRIT13009-L and pRIT13134-L. Transformants carrying one or several copies of each vector were identified. In each case, copy number was estimated by Southern blot analyses of genomic DNA preparations as described above for the vector pRIT13133-L. Digestions at restriction sites that are unique in the vectors (EcoRI for pRIT13133-L, ClaI for pRIT13009-L and pRIT13134-L) were performed, and the same HBV specific DNA probe was used.

Analyses of genomic DNA demonstrates that HBsAg expression cassettes are not rearranged after integration of the vector. Internal PstI-SacII fragments from genomic DNA of transformants carrying several vector copies have the expected size (using HBsAg, TDH3 or ARG3 DNA probes). Transcriptional analyses were performed, and showed synthesis of the three HBsAg mRNA species of the expected sizes. No other vector transcripts, such as run-through transcripts, were observed.

EXAMPLE 3

Production of HBsAg (S,M) Mixed Structures Using Strains Synthesizing Simultaneously the Different Surface Proteins Having characterized series of transformants carrying different copy numbers of a given expression cassette in the isogenic *S. cerevisiae* haploids 10S69d (a) and 10S69d (α), selected haploids were mated to obtain diploids carrying two different expression cassettes, each in its preselected copy number.

A haploid transformant Y748 containing 4 to 5 copies of vector pRIT13133-L (S expression cassette) and the haploid transformant Y728 containing 1 copy of vector pRIT13009-L (M expression cassette) were mated to give the diploid strain Y729 which thus carries 4 to 5 copies of the S expression cassette together with 1 copy of the M expression cassette.

Cells, grown in YNB 2% glucose (with tryptophan 100 μg/ml) to mid-exponential phase, were collected, washed with cold water, and resuspended in 50 mM sodium phosphate buffer, pH8.1, 4 mM ethylene dinitrilo tetraacetic acid (EDTA), 1% Tween 20, 4 mM polymethylsulfonamide (PMSF), and 10% propanol-2. The ratio of buffer volume to wet weight of cells was 1–2 to 1. Cells were broken by passing two times through a French Press at 20,000 psi, and cellular debris removed by centrifugation for 30 minutes at 16,000 g. Crude cell extracts were centrifuged to equilibrium in 1.5 M CsCl, 25 mM sodium phosphate buffer, pH 7.4. Gradients were fractionated.

Each fraction was analyzed for HBsAg antigenicity using the AUSRIA$^R$ test [Abbott Lab] performed according to manufacturer's instructions. The AUSRIA$^R$test assays only assembled surface proteins, not protein monomers. A peak of HBsAg antigenicity is observed at a density of 1.18–1.19 g/cm$^3$ in the CsCl gradient of the Y748 extract, while the Y728 extract gives a peak at a slightly higher density of 1.20–1.21 g/cm$^3$. The Y729 extract gives a peak of AUSRIA$^R$ activity of intermediate density.

Each fraction was also analyzed for the presence of surface proteins by immunoblot as follows: After sodium dodecylsulfate polyacrylamide gel electrophoresis (SDS-PAGE) according to Laemmli, *Nature*, 227:680 (1970) and blotting to nitrocellulose according to Towbin et al, *Proc. Natl. Acad. Sci.. USA*, 76:4350 (1979), the sheet was incubated with a monoclonal antibody, RF6, [Royal Free Hospital, London] directed against a denaturation and reduction resistent epitope localized in the S moiety of the HBsAg envelope proteins. Detection of the immune reaction was by the biotin-streptavidin peroxidase method [Amersham, UK]. Immunoblot analysis of the gradient fractions showed a perfect correlation between the presence of HBV surface proteins and AUSRIA$^R$ activity in each of the three gradients, indicating that the vast majority of HBV surface proteins in the crude extract are present in a lipoproteic structure.

The immunoblots show that the AUSRIA$^R$ active peak obtained from the Y748 extract contains the expected 23 kd band corresponding to the S protein. Additionally, the peak obtained with Y728 contains a 33 kd and 30 kd band, the N-glycosylated and unglycosylated form of the M protein. The AUSRIA$^R$ active peak obtained with the extract from the diploid strain Y729 contains the 33, 30 and 23 kd species. The results with Y748 and Y728 are identical to published results obtained when the S and M expression cassettes were not integrated into the genome but present on 2μ derived plasmids [Harford et al, "Expression of Hepatitis B Surface Antigen in Yeast", In Develop. Biol. Standard. Second WHO/IABS Symposium on Viral Hepatitis, Standardization in Immunoprophylaxis of Infections by Hepatitis B Viruses, Athens, Greece (1982), Edt. S. Karger, Basel 54: 125–130 (1983): Rutgers et al, cited above]. The S and M protein are expressed and assembled into S and M protein particles, respectively.

The following procedure was performed to determine whether the Y729 derived AUSRIA$^R$ active material was a mixture of S and M protein particles, each of homogeneous subunit composition, or a single population of particles of mixed subunit composition. CsCl peak fractions of each gradient containing the envelope proteins as judged by immunoblot were pooled and dialyzed against phosphate buffered saline (PBS). The concentration of the envelope proteins in the dialyzed material was quantified by immunoblot of two-fold serial dilutions of the samples. Based on this quantification, samples containing equivalent amounts of S protein and also equivalent amounts of M and/or L protein were prepared.

Immunoprecipitation was performed with a monoclonal antibody (Mab) specific for either the preS2 region, Mab S2.4 or Mab S2.9 [SmithKline Biologicals, Rixensart, Belgium], the N-glycosylated form of the yeast derived L and M protein preS2 region, Mab Q19/10 [University of Gottingen, FRG] or the preS1 region, Mab S1.1 [SmithKline Biologicals, Rixensart, Belgium] of the envelope proteins. These domain specific Mabs were prepared by standard techniques, e.g., by fusing spleen cells from an animal immunized with 22 nm particles derived from plasma, with a continuous cell line such as a myeloma line, and selecting clones which produce Mabs specific for a given region.

Immune complexes were captured by formalin-fixed *Staphylococcus aureus* (Staph A) cells [Immuno-precipitin, BRL, Gaithersburg, Md., USA]. Rabbit anti-mouse serum was used as sandwich between the Mab and the Staph A cells. Staph A cells were pretreated as recommended by the supplier and finally washed and resuspended (10% w/v) in PBS. To the samples (500 μl each) of envelope protein particles and a control sample of PBS only, washed Staph A cells (20 μl) were added and the mixture was incubated for 30 minutes at room temperature.

After centrifugation, preS specific Mab was added to the supernatant and incubation was for 2 hours at room temperature. Then 20 μl of Staph A-rabbit anti-mouse complex was added and incubation continued overnight at 4° C. Immune complexes were collected by centrifugation, washed five times with PBS containing 0.05% Tween 20 and the final pellet was resuspended in sample buffer for SDS-PAGE. The immune precipitates were then analyzed by immunoblot as described above.

As a control, S protein particles were mixed with M protein particles in a ratio comparable to the one observed for the proteins present in the Y729 derived particles. The S protein derived from Y729 cells is coprecipitated with the M protein, while the S protein derived from Y748 cells or the S protein present in the mixture of S and M protein particles is not precipitated. The immuneprecipitation reaction removes the majority of S protein from the solution of the Y729 derived particles. In contrast, the S protein remains in the supernatant of the immuneprecipitation reaction on the mixture of the S and M protein particles.

Immuneprecipitation with Mab Q19/10 which is specific for a N-glycosylation dependent preS2 epitope gave identical results. This demonstrates that at least a large amount of S protein synthesized in Y729 cells is coassembled with M protein into particles of mixed (S,M) subunit composition.

EXAMPLE 4

Formation of (S,L) and (S,M,L) Mixed Structures

Co-expression of S and L protein was analyzed as described above. Yeast extracts from the *S. cerevisiae* haploid transformant Y957 containing 5 to 7 copies of vector pRIT13133-L (S expression cassette), the haploid transformant Y1034 containing 3 or 4 copies of vector pRIT13134-L (L expression cassette), and the diploid Y1044 formed by mating these haploids, were subjected to CsCl equilibrium centrifugation.

AUSRIA$^R$ activity was found in a peak at a density of 1.18, 1.20 and 1.19 g/cm$^3$ for the Y957, Y1034 and Y1044 extracts, respectively. Immunoblots confirmed the HBsAg antigenicity profile and showed the AUSRIA$^R$ peaks to contain the 23 kd S protein (Y957 extract), the 38 kd and 45 kd unglycosylated and glycosylated forms of the L protein (Y1034 extract), and both the S and L protein species in the Y1044 derived peak. While the L protein species from the Y1034 extract bands at a higher density than the Y957 derived S protein, the L protein species derived from Y1044 have shifted their position to a lower density coinciding with the S protein position.

Immuneprecipitation of the CsCl derived lipoprotein structures with the preS-specific Mab described in Example 3 showed that the S protein derived from Y1044 cells is co-precipitated with the L proteins while the S protein derived from Y957 cells or the S protein present in the mixture of S and L lipoprotein structures is not precipitated. Analysis of the supernatants of the immune precipitation reaction showed that the S protein is efficiently removed from the solution of Y1044 derived lipoprotein structures. Identical results were obtained with Mab Q19/10, demonstrating that co-expression of S and L proteins leads to coassembly into mixed (S,L) lipoprotein structures.

Formation of (S,M,L) mixed structures was demonstrated in a similar way. An established (S,M) producing haploid strain was mated with an L producing strain. Immuneprecipitations with anti-preS1 and anti-preS2 antibodies were performed as described above for the demonstration of (S,M) and (S,L) structures. Results show the presence of (S,M,L) mixed structures in the extract of the diploid strain.

EXAMPLE 5

Control Over the Relative Amounts of the Envelope Proteins by Variation of the Relative Copy Numbers of the Expression Cassettes As described in the above examples, Ty1 linear expression vectors were found to be integrated at a series of Ty1 chromosomal loci. Haploid transformants, each carrying several vector copies at a particular locus have been obtained by screening series of transformants. Therefore, an increase in copy number can be obtained by classical genetics, allowing variation of the relative copy number of the different expression cassettes. Therefore, the mixed particle composition may be varied and controlled by increasing the number of expression cassettes in each vector.

EXAMPLE 6

Antigenicity and Immunogenicity Testing of Particles

Particles of this invention containing two different proteins (M and S peptides) on the same particle were tested for their antigenicity and their immunogenicity in Balb/c mice. In these different assays, HBS (S) and HBS (M) particles were used respectively as negative or positive controls. The antigenicity was analyzed with anti-S, RF1 and RF6 [H. Thomas, Royal Free Hospital, London] and anti-preS2, S2.7, S2.10, and S2.5 [Smith Kline Biologicals] Mabs in ELISA tests.

The particles in serial dilutions were captured by anti-S polyclonal antibodies [Enzygnost-Behring] and detected by the different Mab. HBS (S), HBS (M) and HBS (S,M) particles react very well with the two anti-S monoclonal antibodies, RF1 and RF6. For the preS2 epitopes, only the HBS (M) and HBS (S,M) present a reactivity with the S2.5, S2.7 and S2.10 Mab. The HBS (S) did not give a reaction above the background value.

The immunogenicity of HBS(S,M) particles of this invention [batch 87/04 (3) in Table II below] was studied in Balb/c mice after injection of 1 μg of antigen (protein)/mouse at days 0 and 30. The bleeding of mice was done at day 45 and the different assays performed on individual sera. Controls included HBS(S) particles [batch HB0158 (1) in Table II below] and HBS(M) particles [batch 35-26 (2) in Table II below] adsorbed on Al(OH)$_3$. Anti-HBS antibodies were measured with the AusAb kit [Abbott, USA]and expressed in mIU/ml using the Hollinger formula [Hollinger et al, in Szumness et al eds, "Viral Hepatitis", Philadelphia: Franklin Institute Press 451–466 (1982)].

Anti-preS2 antibodies were measured using an ELISA-inhibition assay. Briefly, serial dilutions of the serum were incubated with HBS (M) particles adsorbed to polystyrene wells of a microplate. After washing, the Mab S2-5 (anti-PreS2 Mab) conjugated to peroxidase (PO) was added to each well. The anti-preS2 antibody present in the serum analyzed competes with S2.5-PO for the same epitope if their antibody specificity is the same. The OD of each unknown sample was transformed in equivalent Mab (mcg/ml) using a standard curve obtained with the purified S2.5.

The individual anti-HBS antibody titers after two injections of antigen (the particles or controls identified above) in Balb/c mice are shown in Table II below. The individual anti-preS2 antibody titers after injection of antigen in Balb/c mice are shown in the Table III below. In these Tables, if the titer was below the cut-off value, it was given a value of 5 for the calculation of GMT.

TABLE II

| | Anti-HBS Antibody Titers (mIU/ml) | | | |
|---|---|---|---|---|
| Mouse | Negative Controls | HB0158 (1) | 35-26 (2) | 87/04 (3) |
| 1 | 6.4 | 36950 | 48889 | 184254 |
| 2 | 3.7 | 6844 | 9250 | 114780 |

TABLE II-continued

| | Anti-HBS Antibody Titers (mIU/ml) | | | |
|---|---|---|---|---|
| Mouse | Negative Controls | HB0158 (1) | 35-26 (2) | 87/04 (3) |
| 3 | 0.0 | 30403 | 966 | 38199 |
| 4 | 2.6 | 3172 | 3715 | 60993 |
| 5 | 5.9 | 3438 | 82950 | 69028 |
| 6 | 10.1 | 120449 | 3853 | 7596 |
| 7 | 8.8 | 38361 | 4055 | 42553 |
| 8 | 2.3 | 17819 | 3254 | 127568 |
| 9 | 0.5 | 9297 | 35819 | 174571 |
| 10 | 4.2 | 7655 | 6530 | 43291 |
| GMT | 3.3 | 14762 | 8326 | 63464 |

TABLE III

| Anti-PreS2 Antibody Titers (mcg/ml equiv.S2.5) | | | |
|---|---|---|---|
| Mouse | HB-0158 | 35-26 | 87/04 |
| 1 | — | 0.2 | 10.2 |
| 2 | — | 17.2 | 15.0 |
| 3 | — | 15.7 | 13.4 |
| 4 | — | 7.1 | — |
| 5 | — | 20.2 | 5.7 |
| 6 | — | 22.9 | 8.9 |
| 7 | — | 17.7 | — |
| 8 | — | 10.7 | — |
| 9 | — | 15.1 | 5.8 |
| 10 | — | 23.6 | 13.8 |
| GMT | — | 15.1 | 8.0 |

The above results show that (S,M) mixed particles are immunogenic and induce the production of antibodies against S and preS epitopes.

EXAMPLE 7

Bordetella pertussis Toxin—Production of the Complete Toxin in vivo in S. cerevisiae The B. pertussis toxin is assembled as a hexamer, containing five different subunits: S1, S2, S3, S4 and 5, S4 being present in two copies per toxin [Tamura et al, *Biochem.,* 21:5516 (1982)]. Genes encoding the five subunits are constructed in expression cassettes for expression in *S. cerevisiae* by conventional methods. The same or different promoters are used, and the resulting expression cassettes are inserted into 5 different Ty vectors according to the invention. These vectors are introduced independently in *S. cerevisiae* strains using similar methods to those described for HBsAg expression cassettes.

Appropriate expression levels for the 5 subunits are obtained by using different appropriate promoters and/or by adapting each vector copy number in order to obtain the correct subunit dosage.

EXAMPLE 8

HIV gp160—Simultaneous Production in *S. cerevisiae* of Antigens From Different Isolates and Formation of "Rosettes" Containing a Mixture of These Proteins The gp120 or gp160 HIV envelope proteins are likely essential constituents in an effective AIDS vaccine. The variations observed in different viral isolates are important and seem to be concentrated in the envelope protein-encoding region. An efficient vaccine may be developed according to the present invention taking into account this extensive heterogeneity and including envelope antigens encoded by different viral isolates. The gp160 antigen of HIV could assemble in "rosettes" similar to those reported for type C retrovirus envelope proteins, [see, Schneider et al, *J. Virol.,* 29:624 (1979); Schneider et al, *Z. Naturforsch,* 36:353 (1981); Schneider et al, *J. Gen. Virol.,* 64:559 (1983)]. The gp160 protein produced in *S. cerevisiae* according to this invention may be obtained as such structures.

Thus using the methods described above a series of gp160 isolates may be produced simultaneously in the same strain of *S. cerevisiae*, in order to obtain "rosettes" structures containing a mixture of these different gp160 proteins. A series of Ty vectors, each containing an expression cassette encoding one isolate of gp160 may be constructed and introduced into *S. cerevisiae* strains, using conventional methods of construction of expression cassettes and following the methods of the present invention.

EXAMPLE 9

Recipient Yeast Strains for Transformation with Ty Linear Vectors Carrying the CUP1 Selective Marker Two *S. cerevisiae* cupe1▲ haploid strains (CUP1 gene disrupted in a strain containing a single copy of that gene) are preferred as recipient yeast strains in the method of the present invention. These strains have the respective genomes: EJ cup1▲ 3d (ura 3, leu 2, trp 1, gal 1▲, cup 1▲, a) and EJ cup 1▲7b (ura 3, trp 1, gal 1▲, cup 1▲, α). These strains were constructed from a strain JWG 32-11 C (trp1, leu 2-3, 2-112, ura 3-52, can$^R$, Cup1: URA 3, α). A stable ura 3 spontaneous mutant was selected and was subsequently crossed with a prototrophic strain 3962 C (a) [J. M. Wiame]. Segregants EJ cup 1▲ 3d and EJ cup 1▲7b were selected for their high efficiency of transformation with Ty linear vectors.

These strains were used for integration of vectors pRIT13034-L and pRIT13134-L, previously described herein. URA3 transformants were isolated, and screened for resistance to copper toxicity. The more resistant transformants appeared to contain 2 to 5 copies of integrated vectors. By classical genetics, strains were obtained carrying higher vector copy numbers, as described above for the strain 10S69d transformed with pRIT13133-L. TRP+ revertants of LEU2 segregants carrying several copies of vectors integrated at several loci were shown to produce high levels of S, L or (S, L) particles, and grew well in fermentors.

The above description and examples are illustrative and not limiting of the invention. For example, the X and Y polypeptides may be other than those described in the examples above. The S, M and L proteins may be employed in modified form to construct a more desireable mixed particle for vaccine use. In addition other polypeptides may be employed in the methods of the invention to generate mixed particles of appropriate composition for vaccine use. Additional known vector components may be employed to replace the specific marker genes, promoters and linker sequences and the like employed in the examples. This invention encompasses all improvements and modifications falling within the scope of the following claims.

What is claimed is:

1. A method for producing a hepatitis B surface antigen particle comprising coexpressing in a yeast cell a first gene encoding a first protein S and a second gene encoding a second protein X-S, wherein S is substantially the major surface protein of hepatitis B virus and wherein X is all or a portion of the preS1S2 polypeptide of hepatitis B virus optionally fused to another polypeptide.

2. The method according to claim 1 further comprising coexpressing a third gene encoding a third protein Y-S, wherein Y is all or a portion of the preS1S2 polypeptide optionally fused to another polypeptide, provided Y is not X.

3. The method according to claim 1 further comprising culturing said yeast cell in an appropriate culture medium and isolating said particle from a cell lysate or extract of said culture.

4. The method according to claim 1 wherein said particle comprises the S protein and an M protein of HBsAg or modified versions thereof.

5. The method according to claim 1 wherein said particle comprises the S protein and an L protein from HBsAg or modified versions thereof.

6. The method according to claim 1 wherein said particle comprises the S protein, an M protein and an L protein from HBsAg or modified versions thereof.

7. The method according to claim 1 wherein S is the 226 amino acid mature surface protein of hepatitis B virus.

8. The method according to claim 1 wherein X comprises an epitope of a pathogenic microorganism, virus, or cell.

9. The method according to claim 1 wherein X is a circumsporozoite protein of Plasmodium or an immunogenic derivative thereof, an HIV protein or an immunogenic derivative thereof, an influenza virus protein or an immunogenic derivative thereof, or epitopes of HBV core antigen.

10. The method according to claim 1 wherein X is all or part of a protein which functions to induce an antibody response; or all or part of a protein which functions as a Tc (cytotoxic T cell) or Th (helper T cell) epitope.

11. The method according to claim 1 wherein X or Y is a functional domain of a biologically active enzyme or protein.

12. The method according to the claim 9 wherein X is all of part of the HIV envelop proteins gp160 and gp120; or proteins derived from the HA2 subunit of the HA protein of influenza virus.

13. The method according to claim 1 wherein the yeast is selected from the group consisting of Saccharomyces, Hansenula and Pichia.

14. The method according to claim 13 wherein said yeast is *S. cerevisiae*.

15. The method according to claim 1 comprising integrating by homologous recombination in said yeast cell a first Ty transposon expression vector carrying the coding sequence for S and a second Ty vector carrying the coding sequence for X-S.

16. The method according to claim 1 wherein said coexpression step comprises cotransformation said yeast with a first vector encoding a protein comprising the S protein and a second vector encoding a protein comprising X-S.

17. The method according to claim 14 further comprising cotransforming said yeast cells by integrating by homologous recombination a third Ty vector encoding a protein comprising Y-S.

18. The method according to claim 2 further comprising cotransforming said yeast cells by integrating by homologous recombination a first vector encoding a protein comprising the S protein, a second vector encoding a protein comprising X-S and a third vector encoding a protein comprising Y-S.

19. The method according to claim 17 wherein said S, X-S and Y-S coding sequences are carried in compatible vectors.

* * * * *